(12) United States Patent
Platt et al.

(10) Patent No.: US 8,367,638 B2
(45) Date of Patent: Feb. 5, 2013

(54) GALACTOSE-PRONGED POLYSACCHARIDES IN A FORMULATION FOR ANTIFIBROTIC THERAPIES

(75) Inventors: David Platt, Newton, MA (US); Eliezer Zomer, Newton, MA (US); Anatole Klyosov, Newton, MA (US)

(73) Assignee: Galectin Therapeutics Inc., Norcross, GA (US)

( * ) Notice: Subject to any disclaimer, the term of this patent is extended or adjusted under 35 U.S.C. 154(b) by 0 days.

(21) Appl. No.: 13/333,497

(22) Filed: Dec. 21, 2011

(65) Prior Publication Data

US 2012/0157407 A1 Jun. 21, 2012

Related U.S. Application Data

(62) Division of application No. 11/749,728, filed on May 16, 2007, now Pat. No. 8,236,780.

(60) Provisional application No. 60/747,313, filed on May 16, 2006.

(51) Int. Cl.
*A61K 31/736* (2006.01)
*C08B 37/00* (2006.01)

(52) U.S. Cl. .................. 514/54; 536/114; 536/123.1

(58) Field of Classification Search .................. None
See application file for complete search history.

(56) References Cited

U.S. PATENT DOCUMENTS

| | | | |
|---|---|---|---|
| 5,895,784 A | 4/1999 | Raz et al. | |
| 6,329,422 B1 | 12/2001 | Fischer et al. | |
| 6,413,494 B1 | 7/2002 | Lee | |
| 6,417,173 B1 | 7/2002 | Roufa et al. | |
| 6,573,245 B1 | 6/2003 | Marciani | |
| 6,642,205 B2 | 11/2003 | Klyosov | |
| 6,645,946 B1 | 11/2003 | Klyosov | |
| 6,652,856 B2 | 11/2003 | Gotwals et al. | |
| 6,756,362 B2 | 6/2004 | Roufa et al. | |
| 6,787,521 B2 | 9/2004 | Culler et al. | |
| 6,812,230 B2 * | 11/2004 | Horuk | 514/255.01 |
| 6,844,354 B1 | 1/2005 | Iizuka et al. | |
| 6,893,637 B1 | 5/2005 | Gilbertson | |
| 6,914,055 B2 | 7/2005 | Klyosov | |
| 6,936,618 B2 | 8/2005 | Dormer et al. | |
| 6,964,761 B1 | 11/2005 | Condos et al. | |
| 6,982,255 B2 | 1/2006 | Klyosov | |
| 6,986,995 B2 | 1/2006 | Rose et al. | |
| 7,012,068 B2 | 3/2006 | Klyosov | |
| 7,491,708 B1 | 2/2009 | Platt | |
| 7,893,252 B2 | 2/2011 | Platt | |
| 2003/0064957 A1 * | 4/2003 | Klyosov et al. | 514/54 |
| 2006/0024357 A1 | 2/2006 | Carpenter et al. | |
| 2006/0067927 A1 | 3/2006 | Chandrasekaran et al. | |
| 2006/0074050 A1 | 4/2006 | Chang et al. | |
| 2006/0105063 A1 * | 5/2006 | Hann et al. | 424/744 |

FOREIGN PATENT DOCUMENTS

| | | |
|---|---|---|
| RU | 2240123 | 11/2004 |
| WO | WO2005020900 | 3/2005 |
| WO | WO2005025501 | 3/2005 |
| WO | WO2005037293 | 4/2005 |

OTHER PUBLICATIONS

Sakon et al., "Combined Intraarterial 5-Fluorouracil and Subcutaneous Interferon-alpha Therapy for Advanced Hepatocellular Carcinoma with Tumor Thrombi in the Major Portal Branches" Cancer (2002) vol. 94 No. 2 pp. 435-442.*

Im et al., "Identification of optimal molecular size of modified Aloe polysaccharides with maximum immunomodulatory activity" International Immunopharmacology (2005) vol. 5 pp. 271-279.*

Bataller R. et al. "Liver Fibrosis" The Journal of Clinical Investigation, 2005, vol. 115, No. 2, pp. 209-218.

Desmouliere et al. "Tissue Repair, Contraction, and the Myofibroblast," Wound Repair and Regeneration. 13(1): 7-12 (2005).

Fitzner et al. "Galectin-1 is an inductor of pancreatic stellate cell activation" Cellular Signaling, 2005, 17: 1240-1247.

Friedman, S.L. "Hepatic Fibrosis: Chapetr10, Diseases of the Liver", Schiff, Sorrell and Maddrey eds. $8^{th}$ Edition, 1999.

Friedman, S.L. "Liver Fibrosis—From Bench to Bedside," Journal of Hepatology. 38: S38 (2003).

Friedman, S.L. "Mechanisms of Disease: Mechanisms of Hepatic Fibrosis and Therapeutic Implications," Nature Clinical Practice: Gastroenterology & Hepatology 1(2): 98 (2004).

Friedman, S.L. "Molecular Regulation of Hepatic Fibrosis, an Intergrated Cellular Response to Tissue Injury," Journal of Biological Chemistry. 275: 2247 (2000).

Hetzel et al. "Different Effects of Growth Factors on proliferation and Matrix Production of Normal and Fibrotic Human Lung Fibrobalsts", 2005, Lung, 225-237.

Gillissen et al. "Characterization of N-Acetylcysteine and Ambroxol in Anti-Oxidant Therapy," Respiratory Medicine. 92: 609-623 (1998).

Kasper et al. "Immunocytochemical Evidence for a Modulation of Galectin 3 (Mac-2), a Carbohydrate Binding Protein, in Pulmonary Fibrosis," Journal of Pathology. 179(3):309-319 (1996).

Lopez et al. "Inhibition of Chronic Airway Inflammation and Remodeling by Galectin-3 Gene Therapy in a Murine Model," Journal of Immunology, Feb. 1, 2006;176(3):1943-50.

(Continued)

*Primary Examiner* — Eric S Olson
(74) *Attorney, Agent, or Firm* — Greenberg Traurig, LLP

(57) ABSTRACT

Methods and compositions for reducing fibrosis and cirrhosis are provided in which an effective dose of an admixture of a polysaccharide compound and, for example, a compound selected from the group consisting of antibodies specific to intracellular or cell-surface: (i) beta-PDGF receptors; (ii) synaptophysin; (iii) zvegf3; (iv) CCR1 receptors; (v) connective tissue growth factor; (vi) alpha 1-smooth muscle actin; (vii) matrix metalloproteinases MMP 2 and MMP9; (viii) matrix metalloproteinase inhibitors TIMP1 and TMP2; (ix) integrins; (x) TFG-β1; (xi) endothelin receptor antagonists; and (xii) collagen synthesis and degradation modulating compounds; (xiii) actin synthesis and degradation modulating compounds; and (xiv) tyrosine kinases is administered to an animal in order to treat fibrosis.

9 Claims, 4 Drawing Sheets

OTHER PUBLICATIONS

Maeda et al, "Stimulation of Proliferation of Rat Hepatic Stellate Cells by Galectin-1 and Galectin-3 through different Intracellular Signaling Pathways", Jouranl of Biol. Chem. 2003, vol. 278, No. 21, pp. 18938-18944.

The Merck Manual of Diagnosis and Therapy (17$^{th}$ edition), 1999, Published by Merck Research Laboratories. pp. 372-374 (1999).

The Merck Manual of Diagnosis and Therapy (19$^{th}$ edition), 2011, Chapter 3: Hepatic and Bilary Disorders, pp. 205-280, Published by Merck Sharp & Dohme Corp., Whitehouse Station, NJ.

di Mola et al. "Connective Tissue Growth Factor is a Regulator for Fibrosis in Human Chronic Pancreatitis," Annals of Surgery. 230(1): 63 (1999).

Nergard et al., "Structural and Immunological Studies of a Pectic Arabinogalactan from Vernonia Kotschyana Sch. Bip. Ex. Walp. (Asteraceae)," Carbohydrate Research. 340: 115-130 (2005).

Ouchi T et al. "Synthesis and Cytotoxic Activity of Oxidized Galactomannan/ADR Conjugate" Journal of Macromolecular Science, Part A: Pure and Applied Chemistry vol. 34, Issue 6, 1997.

Renard et al. "Structure of the Repeating Unites in the Rhamnogalacturonic Backbone of Apple, Beet and Citrus Pectins," Carbohydrate Research. 275: 115-130, (1995).

Ruiz-Perez et al. "Modulation of Surgical Fibrosis by Microbial Zwitterionic Polysaccharides", 2005, PNAS, 102 (46): 16753-16758.

Wang et al, "Galectin-1 and Galectin-3 in Chronic Pancreatitis," Laboratory Investigation. 80(8): 1233-1241 (2000).

Wert et al. "Increased Metalloproteinase Activity, Oxidant Production, and Emphysema in Surfactant Protein D Gene-inactivated Mice," PNAS. 97: 5972-5977 (2000).

Yamazaki et al, "Simultaneous Induction of Galectin-3 Phosphorylated on Tyrosine Residue p21 (WAF1/Cipl/Sdil), and the Proliferating Cell Nuclear Antigen at a Distinctive Period of Repair of Hepatocytes Injured by CC14," Biochemical and Biophysical Research Communications. 280(4):1077-1084 (2001).

International Search report and Written Opinion issued in International Application PCT/US2007/069085 mailed Sep. 2, 2008.

Office Action issued in U.S. Appl. No. 11/749,728 mailed on Jun. 1, 2012.

Office Action issued in U.S. Appl. No. 11/749,728 mailed on Feb. 15, 2012.

* cited by examiner

US 8,367,638 B2

GALACTOSE-PRONGED POLYSACCHARIDES IN A FORMULATION FOR ANTIFIBROTIC THERAPIES

RELATED APPLICATIONS

This patent application is a divisional of U.S. application Ser. No. 11/749,728, filed May 16, 2007 now U.S. Pat. No. 8,236,780, which claims priority of Provisional Patent Application Ser. No. 60/747,313, filed May 16, 2006 and entitled "Galactose-Pronged Polysaccharides in a Formulation for Antifibrotic Therapies." Each of the aforementioned applications is incorporated herein by reference in its entirety.

BACKGROUND OF THE INVENTION

Fibrosis is an intermediate result of and a pathological process itself leading from tissue injury through its encapsulation by extracellular matrix to a pathological formation of scar tissue.

Injury leading to fibrosis occurs in response to a variety of chronic insults including alcohol abuse, drugs, toxins, viral hepatitis B and C, some metabolic diseases, foreign objects, such as small mineral or organic particles (e.g., in the lungs), causing chronic and/or permanent tissue irritation, or other hepatic or pulmonary abnormalities. The advanced stage of fibrosis is cirrhosis, defined by the presence of encapsulated nodules, and eventually cancer.

Fibrosis is a systemic response to chronic injury, developing through a series of highly coordinated molecular events, collectively called fibrogenesis. In one example, fibrosis develops as a result of chronic mammalian liver injury. The steps immediately following chronic mammalian liver injury represent a process called "initiation", which in turns are early events of "activation" of hepatic stellate cells. The next step of stellate cells activation is "perpetuation", and this leads to proliferation, fibrogenesis and matrix degradation. Each of these events is accompanied by specific molecular markers, such as collagen I (a marker on fibrosis), alpha 1-smooth muscle actin (a marker on activation of stellate cells), beta PDGF-receptor (a marker on proliferation), matrix metalloproteinases and their inhibitors MMP2, MMP9, TIMP1 and TMP2 (markers on matrix degradation), cytokine TFG-β1 (a marker on fibrogenesis).

Development of fibrosis can be evaluated by the quantitative level of the respective markers. Reduction of fibrosis can be evaluated by the decrease of the level of the respective markers during various stages of fibrosis. Fibrosis can be reduced and reversed. Furthermore, even the advanced stage of fibrosis, cirrhosis, can also be reversed.

SUMMARY OF THE INVENTION

In one embodiment, methods and compositions are provided that relate to the administration of a galactopolysaccharide in a combination with a antifibrotic compound to a subject in a formulation in which fibrosis is reduced.

In another embodiment, a method is provided for treating fibrosis in a subject, by administering an effective dose of a antifibrotic compound to the subject in a formulation containing a suitable polysaccharide, which may include, but is not limited to, a galactomannan, rhamnogalacturonan, arabinogalactan, combining the polysaccharide with the effective dose of a suitable compound to form a mixture; and administering the mixture to the subject.

In another embodiment, the present invention relates to a method for delivering an effective dose of an admixture of a suitable galactose-containing polysaccharide and a compound selected from the group consisting of antibodies specific to cell-surface and/or intracellular: (i) β-PDGF receptors; (ii) synaptophysin; (iii) zvegf3; (iv) CCR1 receptors; (v) connective tissue growth factor; (vi) alpha 1-smooth muscle actin; (vii) matrix metalloproteinases MMP 2 and MMP9; (viii) matrix metalloproteinase inhibitors TIMP1 and TMP2; (ix) integrins; (x) TFG-β1; (xi) endothelin receptor antagonists; and (xii) collagen synthesis and degradation modulating compounds; (xiii) actin synthesis and degradation modulating compounds; and (xiv) tyrosine kinases.

In another embodiment, the present invention relates to a method for delivering an effective dose of an admixture of a suitable galactose-containing polysaccharide and a compound selected from the group consisting of: (i) IL-1; (ii) IL-10; (iii) anti-zvegf3 compounds; (iv) interferon alpha G (alpha 5); and (v) hepatic stellate cell activation inhibiting compounds.

In another embodiment, the present invention relates to a method for delivering an effective dose of an admixture of a suitable galactose-containing polysaccharide and a compound selected from the group consisting of: (i) Vitamin E; (ii) alpha-lipoic acid; (iii) Tetrandrine; (iv) Silymarin and Silymarin derivatives; and (v) Thalidomide and Thalidomide analogs.

In another embodiment, the present invention relates to a method for delivering an effective dose of an admixture of a suitable galactose-containing polysaccharide and a compound selected from the group consisting of: (i) cysteine; (ii) L-cysteine; (iii) L-methionine; (iv) S-adenosyl methionine; (v) S-methyl cysteine; and (vi) N-acetyl cysteine.

In another embodiment, the present invention relates to a method for delivering an effective dose of an admixture of a suitable galactose-containing polysaccharide and a compound selected from the group consisting of: (i) copper chelating compounds; (ii) halofuginone; (iii) β-amino-propionitriles; (iv) Type V cyclic nucleotide phosphodiesterase inhibitors; (v) antiviral compounds; (vi) alcohol abstinence compounds; and (vii) herbal compounds.

In another embodiment, the present invention relates to a method for delivering an effective dose of an admixture of a suitable galactose-containing polysaccharide and a compound selected from the group consisting of: (i) dextran sulfate; (ii) pentosan polysulfate; (iii) chondroitin sulfate; (iv) heparin sulfate; and (v) heparin.

DETAILED DESCRIPTION OF THE INVENTION

Figure 1:
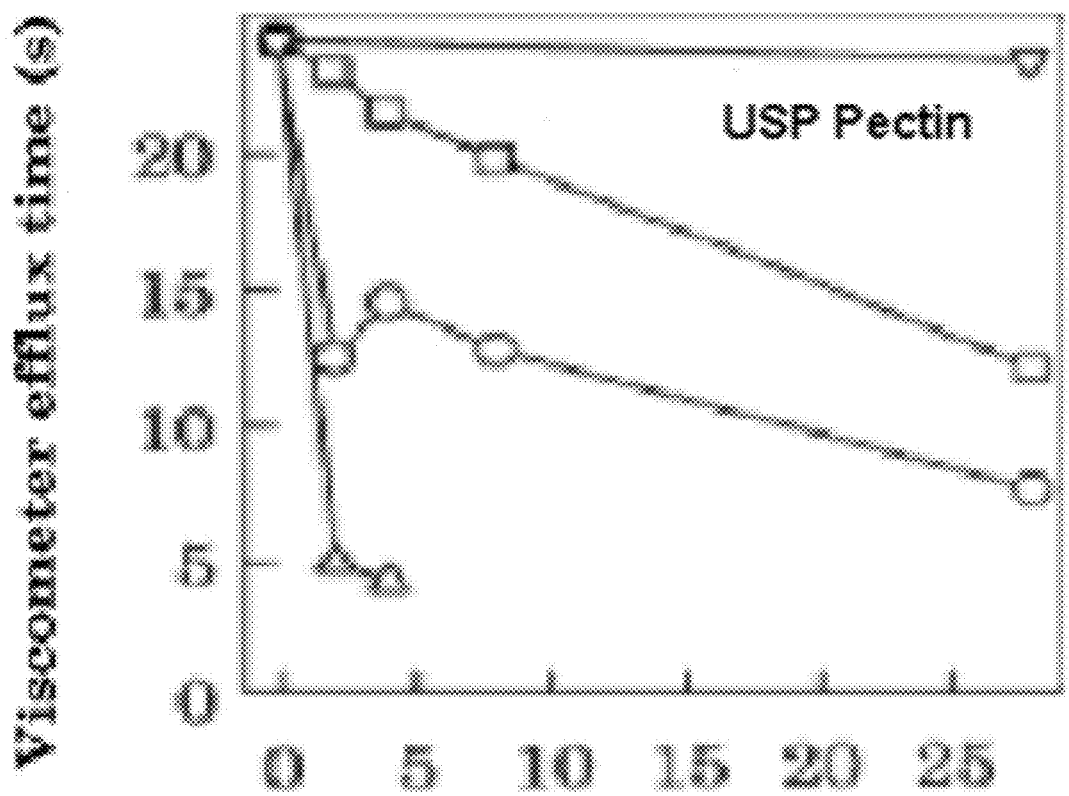
FIG. 1 shows the scission of polysaccharides by ascorbate and/or peroxide ($H_2O_2$). The effect of 10 mM $H_2O_2$ (□), 10 mM ascorbate (○) or 5 mM of each (Δ) is shown.

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and are not restrictive. Therefore, specific structural and functional details disclosed herein are not to be interpreted as limiting, but merely as a representative basis for teaching one skilled in the art to variously employ the present invention.

The following terms shall have the meanings indicated herein and in the claims, unless required otherwise by the context.

"PS" shall mean polysaccharide.

"EHS" shall mean Eaglebreth-Holm Swarm.

"DMEM" shall mean Dulbecco's Soluble branched Eagle's Minimal Essential Medium.

"CMF-PBS" shall mean $Ca^{2+}$- and $Mg^{2+}$-Free Phosphate-Buffered Saline, pH 7.2.

"BSA" shall mean Bovine Serum Albumin.

"galUA" shall mean galactopyranosyl uronic acid, also called galacturonic acid.

"gal" shall mean galactose.

"man" shall mean mannose.

"glc" shall mean glucose.

"all" shall mean allose.

"alt" shall mean altrose.

"ido" shall mean idose.

"tal" shall mean talose.

"gul" shall mean gulose.

"ara" shall mean arabinose.

"rib" shall mean ribose.

"lyx" shall mean lyxose.

"xyl" shall mean xylose.

"fru" shall mean fructose.

"psi" shall mean psicose.

"sor" shall mean sorbose.

"tag" shall mean tagatose.

"rha" shall mean rhamnose.

"fuc" shall mean fucose.

"quin" shall mean quinovose.

"2-d-rib" shall mean 2-deoxy-ribose.

"Administration" refers to oral, or parenteral including intravenous, subcutaneous, topical, transdermal, intradermal, transmucosal, intraperitoneal, intramuscular, intracapsular, intraorbital, intracardiac, transtracheal, subcutaneous, subcuticular, intraarticular, subcapsular, subarachnoid, intraspinal, epidural and intrasternal injection and infusion.

"Subject" is defined here and in the claims as a mammal including a human in need of therapy for, or susceptible to, a condition or its sequalae. The subject may include dogs, cats, pigs, cows, sheep, goats, horses, rats, and mice and humans. The term "subject" does not exclude an individual that is normal in all respects.

"Patient" shall mean a human subject who has presented at a clinical setting with a particular symptom or symptoms suggesting the need for treatment.

"Treatment of fibrosis" refers to prognostic treatment of subjects at high risk of developing a fibrotic or cirrhotic condition as well as subjects who have already developed a fibrotic or cirrhotic condition, regardless of location or type of tissue in which the fibrotic or cirrhotic condition arises.

"Treatment" may also be applied to the reduction or prevention of abnormal cell proliferation, cell aggregation and cell dispersal (metastasis).

"Cirrhosis" refers to any tissue disorder, including such cellular disorders including, but not limited to, renal cirrhosis, liver cirrhosis, ovarian cirrhosis, lung cirrhosis, gastrointestinal or stomach cirrhosis. The term "cirrhosis" refers to an advanced stage of fibrosis, defined by the presence of encapsulated nodules, and eventually cancer. For purposes of this specification and claims, "cirrhosis" is considered to be a type of fibrosis, and is included within the meaning of the term "fibrosis" used herein.

"Fibrosis" refers to any tissue disorder, including, but not limited to, such cellular disorders as, for example, cirrhosis, Kidney fibrosis, liver fibrosis, ovarian fibrosis, lung fibrosis, gastrointestinal or stomach fibrosis, Fibroids. The term "fibrosis" refers to both the pathological process leading from tissue injury through its encapsulation by extracellular matrix, and the result of the process, which is a pathological formation of scar tissue. Fibrosis is a systemic response to chronic injury, developing through a series of highly coordinated molecular events, collectively called fibrogenesis. The steps immediately following chronic liver injury represent a process called "initiation", which in turns are early events of "activation" of hepatic stellate cells. The next step of stellate cells activation is "perpetuation", and this leads to proliferation, fibrogenesis and matrix degradation.

"Molecular markers", or "Biochemical markers", or "Biomarkers", or "Markers" refers to individual molecules of biological origin, which can be monitored as a "readout" of specific metabolic events. These events are accompanied by formation of the "markers", the quantitative level of which can often be used as an indication to advancement of the event. Examples of such markers in fibrosis are collagen I (a marker on fibrosis), alpha 1-smooth muscle actin (a marker on activation of stellate cells), beta PDGF-receptor (a marker on proliferation), matrix metalloproteinases and their inhibitors MMP2, MMP9, TIMP1 and TMP2 (markers on matrix degradation), cytokine TFG-β1 (a marker on fibrogenesis).

"Admixture" means more than one component mixed together to form a combination. For purposes of the present invention, "admixture" means the mixture of two or more compounds at any time prior or subsequent to, or concomitant with, administration.

"Depolymerization" refers to partial or complete hydrolysis of the polysaccharide backbone occurring for example when the polysaccharide is treated chemically resulting in fragments of reduced size when compared with the original polysaccharide.

"Effective dose" refers to a dose of a compound and/or admixture that improves the symptoms of the subject or the longevity of the subject suffering from or at high risk of suffering from cirrhosis. The effective dose in embodiments of this invention can be quantitatively defined as an amount of a polysaccharide compound administered alone or in a mixture with a dose of a antifibrotic compound administered in a subject for treating fibrosis that decreases a level of a chosen molecular marker by at least about 5 percent.

"Saccharide" refers to any simple carbohydrate including monosaccharides, monosaccharide derivatives, monosaccharide analogs, sugars, including those, which form the individual units in an oligosaccharide or a polysaccharide.

"Monosaccharide" refers to polyhydroxyaldehyde (aldose) or polyhydroxyketone (ketose) and derivatives and analogs thereof.

"Oligosaccharide" refers to a linear or branched chain of monosaccharides that includes up to about 10 saccharides units linked via glycosidic bonds.

"Polysaccharide" refers to polymers formed from about 10 to over 100,000 saccharide units linked to each other by hemiacetal or glycosidic bonds. The polysaccharide may be either a straight chain, singly branched, or multiply branched wherein each branch may have additional secondary branches, and the monosaccharides may be standard D- or L-cyclic sugars in the pyranose (6-membered ring) or furanose (5-membered ring) forms such as D-fructose and D-galactose, respectively, or they may be cyclic sugar derivatives, for example amino sugars such as D-glucosamine, deoxy sugars such as D-fucose or L-rhamnose, sugar phosphates such as D-ribose-5-phosphate, sugar acids such as D-galacturonic acid, or multi-derivatized sugars such as N-acetyl-D-glucosamine, N-acetylneuraminic acid (sialic acid), or N-sulfato-D-glucosamine. When isolated from nature, polysaccharide preparations comprise molecules that are heterogeneous in molecular weight. Polysaccharides include, among other compounds, galactomannans and galactomannan derivatives; galacto-rhamnogalacturons and galacto-rhamnogalacturon derivatives, and galacto-arabinogalacturon and galacto-arabinogalacturon derivatives.

"Backbone" means the major chain of a polysaccharide, or the chain originating from the major chain of a starting polysaccharide, having saccharide moieties sequentially linked by either α or β glycosidic bonds. A backbone may comprise additional monosaccharide moieties connected thereto at various positions along the sequential chain.

"Esterification" refers to the presence of methylesters or other ester groups at the carboxylic acid position of the uronic acid moieties of a saccharide.

"Monosaccharides and their derivatives" refers to, within the context of this invention, any of the standard and possible derivatives of monosaccharides (sugars), including but not limited to deoxymonosaccharides, dideoxymonosaccharides, sugar alcohols, sugar acids, sugar esters, sugar ethers, sugar halides, amino sugars, sugar phosphates, pyranose and furanose cyclic forms, open ring forms, sulfonic esters of sugars, glycosidic derivatives, glycols, glycolenes, keto sugars, diketo sugars, protected sugars, acetals such as benzilidenes and ketals such as isopropylidenes, nitro sugars, N-acetyl sugars, N-acetylmuramic acid, and antibiotic sugars such as nojirimycin and dihydronojirimycin.

"Efficacy" of a antifibrotic compound refers to the relationship between a minimum effective dose and an extent of toxic side effects. Efficacy of an compound is increased if a antifibrotic end point can be achieved by administration of a lower dose or a shorter dosage regimen. If toxicity can be decreased, a antifibrotic compound can be administered on a longer dosage regimen or even chronically with greater patient compliance and improved quality of life. Further, decreased toxicity of an compound enables the practitioner to increase the dosage to achieve the antifibrotic endpoint sooner, or to achieve a higher antifibrotic endpoint.

"Pharmaceutically acceptable carrier" refers to any and all solvents, dispersion media, e.g., human albumin or cross-linked gelatin polypeptides, coatings, antibacterial and antifungal compounds, isotonic, e.g., sodium chloride or sodium glutamate, and absorption delaying compounds, and the like that are physiologically compatible. The use of such media and compounds for pharmaceutically active substances is well known in the art. Preferably, the carrier is suitable for oral, intravenous, intramuscular, subcutaneous, parenteral, spinal or epidural administration (e.g., by injection or infusion). Depending on the route of administration, the active compound can be coated in a material to protect the compound from the action of acids and other natural conditions that can inactivate the compound.

In one embodiment, the collagen marker is measured and quantitated by morphometry, using four picrosirius red stained slides per animal. Nine pictures are taken randomly per slide, for a total 36 pictures per animal, which are then evaluated using the BIOQUANT™ image analysis program.

In another embodiment the following markers—alpha 1-smooth muscle actin, beta PDGF-receptor, TGF-beta receptor, MMP1, MMP2, MMP13, TIMP1, TMP2 and collagen I—are assessed using cDNA obtained by reverse transcription from mRNA, extracted from liver tissue.

In one embodiment an effective amount of a polysaccharide compound administered alone or in a mixture with a dose of a therapeutic agent administered in a subject for treating fibrosis is defined as one decreasing a level of a chosen molecular marker by 20 percent.

In another embodiment the effective amount of an administered polysaccharide compound is defined as decreasing a chosen molecular marker between 5 and 50 percent and higher, depending on an advancement of the disease.

In one embodiment, an effective amount of a polysaccharide compound administered alone or in a mixture with a dose of a antifibrotic compound administered in a subject for treating fibrosis is defined as one decreasing a level of a chosen molecular marker by 20 percent.

In yet another embodiment an effective amount of an administered polysaccharide compound is defined as decreasing a chosen molecular marker between 5 and 50 percent and higher, depending on an advancement of the disease.

In another embodiment, if an inducer of fibrosis, such as carbon tetrachloride (subcutaneously) or thioacetamide (intra-peritoneally) administered alone, causes formation of the biochemical markers, but a concurrent administration of the inducer and a suitable polysaccharide including but not limited to galactomannan, rhamnogalacturonan, or arabinogalactan, does not lead to formation of the same marker, or leads to formation of the same marker but in a reduced amount, it can be suggested that said polysaccharide prevents or slows down fibrosis.

In yet another embodiment, if said polysaccharide is administered at later stages of development of fibrosis, and the administration causes reduction of the level of the biochemical markers compared to that in control or to that in the same experimental animal, it can be suggested that the polysaccharide is able to reverse or slow down fibrosis.

In yet another embodiment, if said polysaccharide is administered at later stages of development of fibrosis, and the administration causes reducing of the level of the biochemical markers compared to that in control or to that in the same experimental animal, and then subsequent disappearance of the markers coincides with the return to health of a subject with respect to this particular pathology, it can be suggested that the polysaccharide is able to reverse fibrosis.

In yet another embodiment, if said polysaccharide is administered at the late stages of fibrosis, which can be determined as cirrhosis, and the administration causes a reduction of the level of the biochemical markers compared to that in control or to that in the same experimental animal, it can be suggested that the polysaccharide is able to slow down or reverse cirrhosis.

In yet another embodiment, if said polysaccharide is administered at later stages of development of fibrosis, and the administration causes reduction of the level of the biochemical markers compared to that in control or to that in the same experimental animal by at least approximately 5%, it can be suggested that the polysaccharide is able to reverse or slow down fibrosis.

In one embodiment of the patent a method for treating a fibrosis in a subject is disclosed, comprising administering parenterally an effective dose of a neutral or a cationic polysaccharide compound in an admixture with a dose of a compound to said subject in need thereof in order to treat fibrosis.

In another embodiment the above method is disclosed, wherein the fibrosis is of the liver. In yet another embodiment the method is disclosed, wherein the fibrosis is of the lung. In another embodiment the fibrosis is of the kidneys.

In another embodiment the polysaccharide compound is a rhamnogalacturonan. In another embodiment the polysaccharide compound is an arabinogalactan. In another embodiment the galactomannan has a molecular weight between 20,000 and 400,000 D. In another embodiment the ratio of mannose to galactose in a galactomannan is 1.7:1.

In another embodiment the ratio of mannose to galactose in a galactomannan is 2.2:1. In another embodiment a molecular weight of the rhamnogalacturonan is between 20,000 and 400,000 D. In another embodiment the ratio of galactose to rhamnose in the rhamnogalactan is 3.7:1. In another embodiment the ratio of galactose to rhamnose in the rhamnogalactan is between 0.4 and 6.7 to 1. In another embodiment the arabinogalactan has a molecular weight between 20,000 and 200,000 D. In another embodiment the ratio of galactose to arabinose in the arabinogalactan is between 1.2 and 9.0 to 1.

In a further embodiment of the invention, galacto-rhamnogalacturonate (GR) is a branched heteropolymer of alternating 1,2-linked rhamnose and 1,4-linked GalA residues that carries neutral side-chains of predominantly 1,4-b-D-galactose and/or 1,5-a-L-arabinose residues attached to the rhamnose residues of the RGI backbone. GR side-chains may be decorated with arabinosyl residues (arabinogalactan I) or other sugars, including fucose, xylose, and mannose. These are also referred to in commercial use as pectic material.

In one embodiment, preparation involved modifying naturally occurring polymers to reduce the molecular weight for the desired range, adjusting the alkylated groups (demethoxylation or deacetylation), and adjusting side chain oligosaccharides for optimum efficacy. For example, natural polysaccharides may have a molecular weight range of between about 40,000-1,000,000 with multiple branches of saccharides, for example, branches comprised of 1 to 20 monosaccharides of glucose, arabinose, galactose etc, and these branches may be connected to the backbone via neutral monosaccharides such as rhamnose. These molecules may further include a single or chain of uronic acid saccharide backbone that may be esterified from as little as about 2% to as much as about 30%. The multiple branches themselves may have multiple branches of saccharides, the multiple branches optionally including neutral saccharides and neutral saccharide derivatives creating mainly hydrophobic entities.

An example of a galactomannan is a polysaccharide prepared from guar gum and having a size is in the range of 2000-600,000 D or in the range of 90,000 to 415,000 D or in the range of 20,000-200,000 D. In specific examples, the galactomannan may have an average size molecular weight of 50,000 D or 215,000 D. In a further embodiment of the invention, the galactomannan is isolated from powder obtained from the seed of the plant *Cyamopsis tetragonoloba*.

In a further embodiment, a rhamnogalacturonate has a molecular weight range of 2,000 to 200,000 D. In specific examples, the rhamnogalacturonanate may have an average size molecular weight of 34,000 D or 135,000 D and is obtained through chemical, enzymatic, physical treatments and purification from pectic substance of Citrus peels and apple pomace or soybean hull or alternatively processed from sugar beet pectin.

In further embodiments of the invention, a galactomannan is used to reduce fibrosis under a antifibrotic action of an antifibrotic compound when it is mixed with the compound prior to administration. The galactomannan may be a β-1,4 D-galactomannan. Moreover, the galactomannan may include a ratio of 2.0-3.0 mannose to 0.5-1.5 galactose. The ratio of mannose to galactose may be 2.6 mannose to 1.5 galactose or 2.2 mannose to 0.9 galactose or 1.13 mannose to 1 galactose or 2.2 mannose to 1 galactose.

In a further embodiment, the ratio of galacto-polysaccharide to an antifibrotic compound in the mixture may be in the range of 0.1:1 w/w to 10:1 w/w. In an embodiment of the invention, administration of the mixture results in a reduced fibrosis (as determined by a reduced level of the specific markers) of greater than 20% compared to best standard of therapy. In another embodiment, the galacto-polysaccharide in combination with anti-fibrotic drugs reduced fibrosis by greater than 50% compared with standard care.

A further embodiment of the invention provides a method for use in treating a fibrosis including but not limited to, of the liver, the lungs, the kidneys, the eye, the skin.

In one embodiment, an example of a polysaccharide includes:

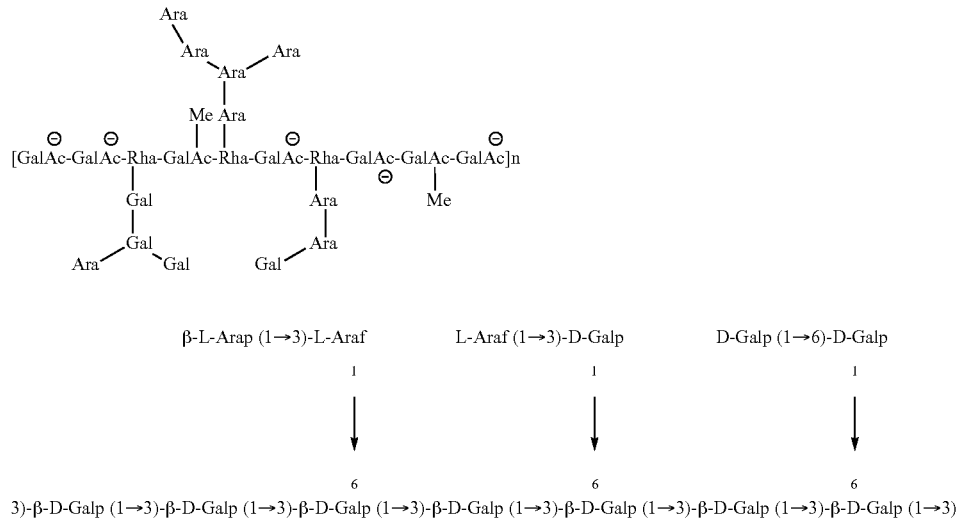

-continued

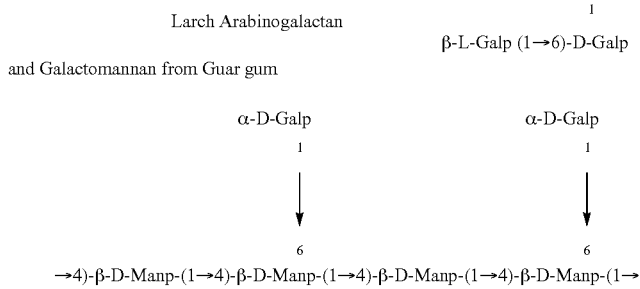

Larch Arabinogalactan
and Galactomannan from Guar gum

In an embodiment of the invention, Galacto-Rhamnogalacturonases (GR) is a branched heteropolymer of alternating a-1,2-linked rhamnose and a-1,4-linked GalA residues that carries neutral side-chains of predominantly 1,4-b-D-galactose and/or 1,5-a-L-arabinose residues attached to the rhamnose residues of the RGI backbone. GR side-chains may be decorated with arabinosyl residues (arabinogalactan I) or other sugars, including fucose, xylose, and mannose. These are also referred to in commercial use as pectic material.

In one embodiment, soluble chemically altered galacto-Rhamnogalacturonases are prepared by modifying naturally occurring polymers to reduce the molecular weight for the desired range, reducing the alkylated group (de-methoxylation or de-acetylation) Prior to chemical modification, the natural polysaccharides may have a molecular weight range of between about 40,000-1,000,000 with multiple branches of saccharides, for example, branches comprised of 1 to 20 monosaccharides of glucose, arabinose, galactose etc, and these branches may be connected to the backbone via neutral monosaccharides such as rhamnose. These molecules may further include a single or chain of uronic acid saccharide backbone that may be esterified from as little as about 2% to as much as about 30%. The multiple branches themselves may have multiple branches of saccharides, the multiple branches optionally including neutral saccharides and neutral saccharide derivatives creating mainly hydrophobic entities.

We describe chemical modification procedures that involves a enzymatic, peroxide and transition metals or peroxide/ascorbate session of the glycosidic bond in the polymer backbone or alkaline reductive depolymerization or controlled into smaller, branched polysaccharide molecules, using controlled conditions of time, temperature and buffer. Treatments (see Example 1, 2, 3). The first purification procedure is extraction of the polysaccharide with alkaline and/or chelation solution to remove proteins, pigments and other impurities.

The following are merely illustrative examples of the production of polysaccharides that are not meant to limit the invention.

EXAMPLE 1

Method of Modifying Naturally Occurring Polysaccharides

A starting polysaccharide is treated with U.V. radiation or suspended in 70% alcohol treatment for about 48 hours to reduce microbial contamination. All further steps are conducted under semi-sterile conditions. After irradiation the polysaccharide is slowly dissolved in distilled water and the amount of total carbohydrate is determined by the phenol sulfuric acid method (Fidler et al., Cirrhosis Res., (1973), vol. 41, pp. 3642-3956.)

A solution in distilled water is prepared at 20 g/L of polysaccharide, starting for example with USP pectin (Pelco) is made and pH is adjusted to pH 5.5 with 1 M sodium succinate, The polysaccharide solutions is then incubated at fix temperature, for example; 20° C. and peroxide and/or ascorbate are added together as in example (FIG. 1) or sequentially.

$H_2O_2$ caused a slow scission of USP Pectin at pH 5.5, at 10 mM (FIG. 1). The half time required to double the specific fluidity was 15±72 h (FIG. 1). L-Ascorbate at same condition and concentration induced faster scission. By far the most dramatic effect, however, was produced by combination of 5 mM ascorbate and 5 mM H2O2 which caused faster scission. Sequential addition of ascorbate to polysaccharide solution already containing even 1 mM $H_2O_2$ caused further stimulation of scission. The rate and extent of scission was determined by the dose of ascorbate added, time of addition post $H_2O_2$ addition, pH and temperature. These indicate that an initial reaction preceded the Scission process. A pH of 4.5, gave the shortest delay and the greatest rate of scission. Thus the enhanced effect of ascorbate depended on $H_2O_2$ or dehydroascorbate produced by the reactions (below).

$$AH_2+O_2 \rightarrow A+H_2O_2$$

or $$AH_2+H_2O_1 \rightarrow A+2H_2O$$

Where AH2 is ascorbate, and A is dehydroascorbate

For example digestion of 20 g/L of USP pectin with 10 mM H2O2 or 10 mM ascorbate or the combination of both at 5 mM each indicate a linear relation between digestion time and the viscometer measurements as below. The kinetics was also well correlated with incubation temperature.

This method can be further enhanced in presence of metals like $Ca^{++}$, $Cu^{++}$ or $Fe^{++}$. The most likely source of cleavage is Fenton reaction (Halliwell, B. and Gutteridge, J. M. C. (1990) Methods Enzymol. 186, 1-85) which generates ionized OH, requires H2O2 and the reduced form of a transition metal ion, Cu+ reported being 60 times more effective than Fe2+.

All the polysaccharide samples usually contained measurable traces of Fe, Cu and Zn in ppm level. The Cu and Fe content was similar in several commercial polysaccharides (as reported in their C of A) and similarly analytical grade ascorbic acid contained low ppm traces of Cu and Fe. Therefore, when no transition metal are deliberately added, the Fenton reactions would be feasible.

$$Cu^{+}+H_2O_2 \rightarrow OH+OH^{-}+Cu^{2+} \qquad (3)$$

EXAMPLE 2

Method of Modifying Naturally Occurring Polysaccharides

The pH of the polysaccharide solution is increased to pH 10 with, for example, 3N NaOH. After short incubation at 5 to 50° C. for 30 to 60 minutes, 10 to 20% ethanol is added and the purified polysaccharide is precipitated. This removed proteins and pigments associated with commercially available polysaccharides. The polysaccharide is then dissolved to a 20 g/L and then an acid is added, for example trifluoroacetic acid at final concentration of 0.01 to 1.0 M has been demonstrated to give a controlled depolymerization. Other acids or combination of them like sulfuric, HCl, Acetate, propionic acid, or methansulfonic acid can be used to shorten the hydrolysis time and improve the yield of a desired structure of branched polysaccharide without oxidation. After appropriate time intervals, for example a time course from 10 minutes to 48 hours, at temperature of 15 to 121° C., the solution is neutralized to pH 3 to 5, cooled to 4° C. and centrifuged to remove any insoluble matter. Then the supernatant is neutralized to a final pH of about 6.0 to 8.0 with 1N NaOH for example, 20% ethanol is added to recover the soluble polysaccharide. Ratio of polysaccharide to acid, type of acid, concentration, pH temperature and time interval are selected so to generate a soluble branched polysaccharide that has a molecular weight of 50 kD, 60, kD, 75 kD, 90 kD, 105 kD, 125 kD, 150 kD, 175 kD, and up to 200 kD. The resulting soluble branched polysaccharide product can further washed with 70% ethanol or with 100% acetone to provide a final dry powder. Thereupon the soluble branched polysaccharide is resolubilized in water to a final concentration of about 5-15% by weight for analytical identification, efficacy or toxicological studies. The soluble branched polysaccharide may be further diluted for use according to embodiments of the invention in which concentrations of 0.01-10% may be provided to cells. Depending on the desired soluble branched polysaccharide composition and molecular weight.

EXAMPLE 3

Method of Modifying Naturally Occurring Polysaccharides

The pH of the polysaccharide solution is increased to pH 9 with, for example, 3N NaOH. After short incubation at 5 to 50 C for 30 to 60 minutes, 10% ethanol is added and the purified polysaccharide is precipitated. This removed proteins and pigments associated with commercially available polysaccharides. Then reducing compound such as a sodium borohydride, lithium borohydrate, sodium cyanoborohydride, sodium triacetoxyborohydride or other borohydrate salts to create a session by alkaline reductive mechanism of the glycosidic bonds. This form fragments of a size corresponding to a repeating subunit. (U.S. Pat. No. 5,554,386). Again temperature and time can be used to shorten the hydrolysis time and improve the yield of polysaccharide. After appropriate time intervals, for example a time course from 30 minutes to 24 hours, at temperature of 25 to 75° C., the solution is cooled to 4° C. and centrifuge to remove any insoluble matter. Then the supernatant is neutralized to a final pH of about 6.0 with 1N HCl for example, 20% ethanol is added to recover the soluble polysaccharide. Ratio of polysaccharide to reductive compound, type of compound, concentration, pH, temperature and time interval are selected so to generate a soluble branched polysaccharide that has a molecular weight of 50 kD, 60, kD, 75 kD, 90 kD, 105 kD, 125 kD, 150 kD, 175 kD, and up to 200 kD. The resulting soluble branched polysaccharide product can further fractionate with 20 to 70% ethanol and finally with 100% acetone to provide a final dry powder. Thereupon the soluble branched polysaccharide is resolubilized in water to a final concentration of about 5-15% by weight for analytical identification, efficacy or toxicological studies. The soluble branched polysaccharide may be further diluted for use according to embodiments of the invention in which concentrations of 0.01-10% may be provided to cells. Depending on the desired soluble branched polysaccharide composition and molecular weight.

The target molecular weight range for the chemically soluble branched polysaccharides is in the range of 50 to 200 kD.

As the temperature (or pH) increases, a so-called β-elimination starts. The β-elimination in present of alkaline borohydrates results in controlled process of chain cleavage accommodated with loss of viscosity and gelling properties, which are used to monitor the reaction

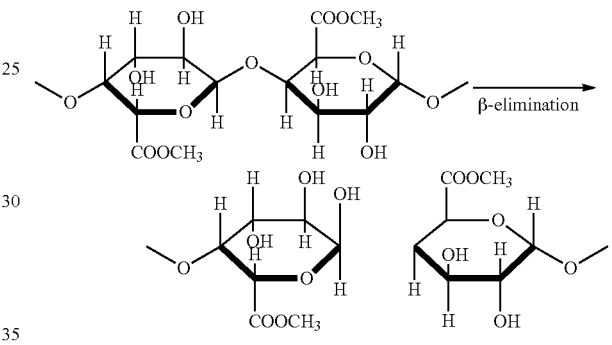

EXAMPLE 4

Galactomannans

For example polysaccharide produced from Guar Gum a powder from seeds of *Cyamopsis tetragonoloba*

We provide a method of treating a subject with a antifibrotic compound that increases the efficacy of the antifibrotic compound. The method requires the co-administration of the compound with a polysaccharide. In addition to increasing efficacy, the co-administration of a polysaccharide with a antifibrotic compound may reduce the toxicity of the compound. In embodiments of the invention, the polysaccharide, galactomannan, has been shown to be effective in increasing the efficacy of antifibrotic compounds when coadministered with the compounds. Although the examples provided herein describe the beneficial effects of galactomannans, we do not exclude the possibility that other polysaccharides may have a similar effect. The increase in efficacy may arise from a synergistic effect between the galactomannan and the antifibrotic compound mixture.

Both the polysaccharide and the antifibrotic compound may separately be formulated, in a dry form for example as a powder, or in a liquid form. In a preferred embodiment, the polysaccharide and antifibrotic compound are mixed prior to administration. The mixture may be in the form of a liquid, a powder or an aerosol.

One of ordinary skill in the art can determine and prescribe the effective amount of the antifibrotic composition required based on clinical protocols. In general, a suitable daily dose of a composition of the invention will be that amount of the composition, which is the lowest dose effective to produce a antifibrotic effect.

Galactomannan is a polymer that may occur in a variety of size ranges. Moreover, the galactomannan may be derivatized or hydrolyzed to result in fragments of the native molecule or may be reacted to provide chemically modified forms of the native molecule. Embodiments of the invention provide a galactomannan having a molecular weight in the range of 20,000-600,000 D. The galactomannan may further have a size in the range of 90-415,000 D or 40,000-200,000 D, or 50,000-80,000 D. Example 1 utilizes a galactomannan with an average molecular weight of 65,000 D while Example 2 utilizes a galactomannan with an average molecular weight of 83,000 D.

The ratio of mannose to galactose may vary according to the source of the galactomannan and the isolation procedure. In embodiments of the invention, the galactomannan may have a mannose to galactose ratio of 2.0-3.0, mannose: 0.5-1.5 galactose. The ratio of mannose to galactose may be 2.6:1.5 or 2.2:0.9 or 1.13:1 or 2.2:1. In Example 1, the ratio of mannose to galactose is 1.7:1 and in Example 2, the selected ratio of mannose to galactose in the galactomannan is 2.2:1.

In one preferred embodiment, the structure of galactomannans is a poly-β-1,4-mannan backbone, with the side substituents bound via α-1,6-glycoside linkages.

EXAMPLE 5

Arabinogalactans

The active galacto-polysaccharide is produced from powder readily available from the wood of the larch tree primarily *Larix occidentalis* (Western Larch). The process in general follow the preparation listed above for rhamnogalacturonate and galactomannan. The target molecular weight is 20,000 to 70,000 D with at least 5% terminal galactose side chain.

The following discussions and examples of assays utilized to demonstrate efficacy and effective dose are to be used as illustrative examples and are not meant to limit the present invention to the examples illustrated.

EXAMPLE 1

Liver, Lung, Kidney and Plasma Distribution of Radiolabeled (Tritiated) Galactomannan in Healthy Male Athymic NCr-nu Mice Twelve male NCr-nu athymic nude mice (Charles Rivers Laboratories, Raleigh, N.C.) were acclimated in the laboratory one week prior to experimentation. The animals were housed in microisolator cages, four per cage, and using a 12-hour light/dark cycle. All animals received sterilized tap water and sterile rodent food ad libitum. The animals were observed daily and clinical signs were noted. The mice were healthy and had not been previously used in other experimental procedures. The mice were randomized and were comparable at the initiation of treatment.

Tritiation of the galactomannan was performed as follows. 12.8 mg of the galactomannan was dissolved in 2.0 mL of water and exposed to 25 Curies of tritium gas in the presence of Pd/BaSO$_4$ catalyst (120 mg, totally insoluble in water). After one hour the gas supply was removed, the catalyst was filtered away, and the aqueous solution of the galactomannan was evaporated to dryness repeatedly (four-fold, adding water), until no labile tritium was found. Total yield of the labeled galactomannan was 3.8 mC$_i$, specific radioactivity was 300 μC$_i$/mg.

All twelve mice were given a single intravenous injection of cold or tritiated galactomannan (either 6 or 60 mg/kg) on the same day. Non-labeled galactomannan was formulated in saline, and tritiated galactomannan was added to the solution so that each animal received 10 μC$_i$ of radioactivity. All dosing solutions (100 μL each) were counted in duplicate. Six mice were injected with 6 mg/kg solution, and six mice—with 60 mg/kg solution.

Two mice from each group were bled at 1, 6, and 24 hrs after injection, and plasma was prepared. Animals were then sacrificed; livers, kidneys and lungs were collected, weighed and flash-frozen for further analysis.

After weighing, livers were dissolved in 10 mL of Soluene 350 and incubated first for 4 hrs at 50° C., and at room temperature, until tissues were solubilized. One mL of the resulting solution was counted in a scintillation counter as a single sample. Based on tissue weight and the sample volume, the number of μC$_i$ of tritiated galactomannan per gram of tissue was calculated.

Kidneys were treated in the same manner, but dissolved in two mL of Soluene. After the tissue was solubilized at room temperature, 15 mL of Safety Solve scintillation fluid was added and samples were incubated overnight. Five mL of the resulting solution were diluted in 15 mL of Safety Solve and counted in a scintillation counter as a single sample. Lungs were treated in the same manner but dissolved in one mL of Soluene. Plasma samples (50 μL each) were placed direct into Safety Solve and counted as a single sample.

The data are shown in Table 1.

TABLE 1

Distribution of radiolabeled galactomannan (at 6 or 60 mg/kg) in tissues of mice

|  | 1 hr after injection | 6 hr after injection | 24 hrs after injection |
|---|---|---|---|
| Liver |  |  |  |
| μC$_i$ of $^3$H- galactomannan per liver, total | 0.262 | 0.196 | 0.169 |
| Same, per 1 g of liver | 0.219 | 0.146 | 0.129 |
| Plasma |  |  |  |
| μC$_i$ of $^3$H- galactomannan per mL of plasma | 0.201 | 0.095 | 0.106 |
| Kidney |  |  |  |
| μC$_i$ of $^3$H- galactomannan per kidney, total | 0.120 | 0.060 | 0.040 |
| Same, per 1 g of kidney | 0.302 | 0.131 | 0.087 |
| Lungs |  |  |  |
| μC$_i$ of $^3$H- galactomannan per lungs, total | 0.019 | 0.012 | 0.011 |
| Same, per 1 g of lungs | 0.117 | 0.063 | 0.060 |

The statistical evaluation was based on experiments to trace and quantify the labeled galactomannan in organs/tissues (liver, kidneys, lung, and plasma). Six mice were treated with galactomannan at 60 mg/kg with each of 2 mice sacrificed at 1, 6, and 24 hours; six mice were treated with galactomannan at 6 mg/kg with each of 2 mice sacrificed at 1, 6, and 24 hours, as described above. The percentages of $^3$H-galactomannan recovered per organ (μC$_i$/gram) was used for analyses; plasma outcome (μC$_i$/ml) was counted from the entire sample.

The assessment of radiolabel uptake was challenging with only two mice per treatment-sacrifice time combination and occasional outliers. To address the number of mice per group, pooling tests were performed for the two galactomannan treatment groups; this would potentially increase sample size per group to four. To address possible outliers, all outcomes for each individual mouse was visually compared to the other mice in the series-treatment-time combination; the four possible mice outcomes were considered in this evaluation since any sigma-based rule would have excluded none or both observations if applied separately to the two different series.

SAS (Version 6.12, Cary, N.C.) was used for all analyses. PROC ANOVA was used for pooling tests, while PROC FREQ was used to estimate means and standard deviations.

It was observed that galactomannan freely binds to liver, kidney, lung, and plasma, and did not reach limits of the binding, e.g. did not reach saturation of the binding between the 6 mg/kg and 60 mg/kg doses. When 6 mg/kg (with a relative radioactivity of 1.0) and 60 mg/kg (with a relative radioactivity of 0.1) doses of galactomannan were administered, the amount of bound radioactive galactomannan was the same; that is, the amount of bound galactomannan increased 10-fold for the 10-times higher dose.

The distribution of radioactivity in whole tissues as well as per weight or volume (in plasma) was practically identical for 6 and 60 mg/kg of galactomannan, hence, the respective data were pooled for Table 1. Overall, the data in Table 1 are average for four animals.

$^3$H-galactomannan elimination from plasma, kidneys, and lungs in the various groups was relatively slow. An average of approximately 50% of the one-hour radioactivity was detected at 6 hours. Elimination of $^3$H-galactomannan from the liver was more gradual than in other tissues, and on average, more than 50% of the radioactivity detected at one hour after injection was still present at 24 hours. This can be compared, for example, with clearance of 5-fluorouracil from the liver, which was eliminated to 1.6% after 24 hrs, and from the lungs and the kidneys, which was eliminated to 3.6% and 3.8%, respectively, for the same period.

EXAMPLE 2

Assessing the Antifibrotic Efficacy of a Modified Galacto-Rhamnogalacturonate Compounds in LX2, an Immortalized Human Hepatic Stellate Cell Line The antifibrotic activity of a galacto-polysaccharides was determined in triplicate, at five concentrations and three time points (4, 12 and 24 hrs) on hepatic stellate cell (HSC) proliferation, employing the method of 3H-Thymidine incorporation, as well as regarding the galacto-polysaccharide effect on the following markers of fibrogenesis:

Collagen I (a marker on fibrosis)
Alpha 1-smooth muscle actin (a marker on activation of stellate cells)
Beta PDGF-receptor (a marker on proliferation)
MMP2, MMP9, TIMP1 and TIMP2 (markers on matrix degradation)
TFG-β1 (a marker on fibrogenesis).

Two more polysaccharides served as reference compounds. They were a galacto-rhamnogalacturonate from citrus, and a galactomannan from guar gum.

LX2 cells, an immortalized human hepatic stellate cell line, were incubated at 370 C in an atmosphere of 5% CO2 in Dulbecco's modified minimal essential medium (Gibco BRL Life Technologies, Rockville, Md.) containing 1% fetal calf serum (FCS), 2 mmol/L of L-glutamine and 5000 IU/mL of penicillin/5000 g/mL streptomycin for 1 to 2 days before starting experiments. They were then serum starved with 0.1% BSA (0.2% FCS) for 24 hours, and treated with each of the three polysaccharides in the following concentrations: galactomannan 0.5-1 mg/ml, citrus galacto-rhamnogalacturonate 0.1-0.5 mg/ml or apple galacto-rhamnogalacturonate 0.1-0.5 mg/ml for 12, 24, 48 and 72 hours. The exact concentrations of each modified polysaccharide was adjusted according to ongoing data during the experiment.

To confirm that the hypothesized reductions in fibrogenic markers were not accounted for by decreasing cell viability, an MTT viability assay was performed. 200 μl of the MTT solution (2 mg of MTT in 1 ml of DMEM) were added to each well of 24-well plate and incubated at 37° C. for 1 hr. After the incubation, the media was discarded and 100 μl of N-propanol added to each well. After 5-10 minutes of reaction, 50 μl of the solution was taken from each well and transferred into 96-well plate and the O.D. was read with ELISA Reader at 570 nm.

To indicate that the effects of the polysaccharides were specific for fibrogenic gene expression, cell proliferation was assessed in the presence of the polysaccharides. Assessment of proliferation is a valuable indicator of stellate cell, activation, and thus compounds that reduce proliferation are expected to reduce the overall number of fibrogenic cells during liver injury, which might be erroneously taken as a specific marker-reducing effect.

Cells were serum starved, then incubated in medium containing 3H thymidine as previously described (22). After washing the cells with cold PBS 3 times, 500 μl of 0.25 N NaOH/0.25% SDS is added to each well of 24-well plate and transferred to Scintillation vials containing 100 μl of 1N HCl. Then 5 ml of Scintillation Solution is then added to the vial and vortexed. CPM is read in Scintillation Counter (LS3801 Liquid Scintillation System, BECKMAN).

The antifibrogenic activity of the polysaccharides was measured by their effect on expression of established fibrotic markers by Quantitative real time RT-PCR of fibrotic marker mRNAs. RNA from LX2 cells was extracted and purified using the Qiagen RNAeasy mini-kit. Concentrations was then measured in Life Science UV/VIS spectrophotometer DU 530 Bekman. Total RNA was reverse transcribed to complementary DNA (cDNA) using the Reverse Transcription System by Promega (Madison, Wis.) (Sprint™ PowerScript™ Double PrePrimed Single Shots, Clontech, USA). One microgram of RNA in 7.7 μl of nuclease-free water was added to 2.5 μl of 10× reverse transcriptase buffer, 10 μl of 25 mM MgCl2, 2.5 μl of 10 mM dNTP, 1μl of random primer, 0.5 μl of RNase inhibitor and 0.8 μl of AMV reverse transcriptase (one microgram of RNA was added into a tube containing reaction mixture which contains 0.5 μg of PowerScript Reverse Transcriptase, 20 μM Random hexamer primers, 20 μM Oligo(dT) 18 primers, 10 mg/ml BSA, 1M DTT, 10 mM dNTP mix, 10× reaction buffer, cryoprotectant and stabilizers). The reaction was performed for 10 min at 25° C. (annealing), 60 min at 42° C. (cDNA-synthesis), and 5 min at 95° C. (enzyme denaturation), 80 min at 42° C., 10 min at 70° C. by PTC-200, Peltier Thermal Cycler.

Real-time quantitative PCR was analyzed in triplicate and performed with ABI Prism 7900HT Sequence Detection System (Applied Biosystems, Foster City, Calif.) LightCyclerR480, Roche, USA. One microliter of cDNA was used in each PCR reaction, Platinum Taq DNA polymerase, Syber green, 100 mM dNTP (Invitrogen Corp, Carlsbad, Calif.) Taq Polymerase, dNTP, DMSO, 25 nM MgCl2, 10× Taq Buffer, NF H2O, Zybo Green, and the fluorescence signals was captured during each of the 40(45) cycles, in proportion to the quantities of double-stranded DNA (denaturation 15 s at 95° C., annealing 15 s at 56° C. and extension 40 s at 72° C.) (1 cycle for denaturation 5 min at 950 C), 45 cycles for amplification (10 sec at 95° C., 10 sec at 55° C., 12 sec at 72° C.), 12 sec at 65° C. for Melting Curve, and 10 sec at 40° C. for Cooling). Detection of the PCR products by agarose gel electrophoresis was used to confirm the homogeneity of the DNA products. GAPDH was used as a reference gene for normalization, and water was be used as negative control.

Relative quantitation was calculated using the comparative threshold cycle (CT) method as described in the User Bulletin, ABI PRISM 7900HT Sequence Detection System (Relative quantification analyses was done using the LightCycleR 480 Relative Quantification Software supplied by the company). CT indicates the fractional cycle number at which the amount of amplified target genes reaches a fixed threshold within the linear phase of gene amplification, and is inversely related to the abundance of mRNA transcripts in the initial sample. Mean CT of duplicate (triplicate) measurements were used to calculate $\Delta$CT as the difference in CT for target and reference (GAPDH) genes. $\Delta$CT for each sample was compared to the corresponding CT of the control experiment and expressed as $\Delta\Delta$CT. Relative quantization was expressed as fold-induction or repression of the gene of interest compared to the control condition according to the formula 2-$\Delta\Delta$CT.

Figure 2:
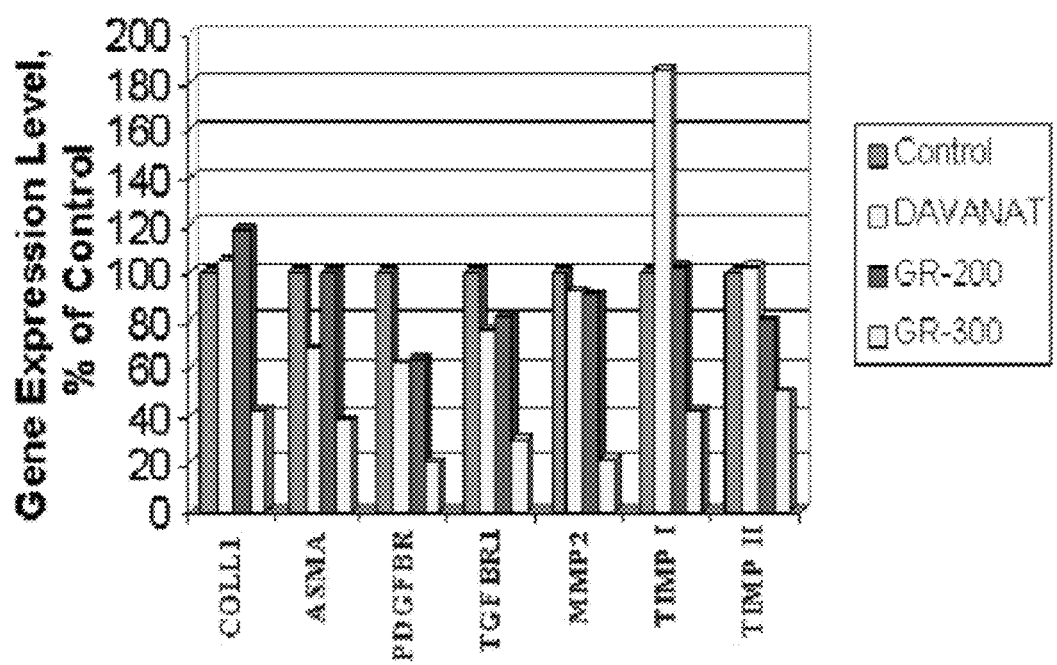
FIG. 2 shows the effect of galacto-polysaccharides' derivatives on molecular markers of fibrogenesis.

A figure below (FIG. 2) shows that the galacto-rhamnogalacturonate (GR-300) suppresses the fibrosis markers' expression between 50% and 80% while the galactomannan (DAVANAT) and the galacto-rhamnogalacturonate (GR-200) decrease fibrosis markers' expression from 0 to 40%. These results indicate a significant antifibrotic effect of the polysaccharides, particularly that of apple origin, on human hepatic stellate cells, and suggest that the polysaccharides can protect from and even reverse the progression of liver fibrosis.

The results (FIG. 2) of qRT-PCR tests for fibrosis markers Collagen I (COLL 1), alpha-1 smooth muscle actin (ASMA), platelet derived growth factor receptor-beta (PDGFBR), transforming growth factor receptor beta-1 (TGFBR1), matrix metalloproteinase 2 (MMP2), tissue inhibitor of metalloproteinase 1 (TIMP I) and tissue inhibitor of metalloproteinase 2 (TIMP II) after 48 hrs as control, and in the presence of 1 mg/ml Davanat, 0.1 mg/ml GR-200 or 0.1 mg/ml GR-300. The results are shown after normalization to GAPDH expression levels as a house keeping gene.

In order to confirm that the observed reductions in fibrogenic markers are not accounted for by decreasing cell viability, an initial MTT cell viability assay was performed on the LX2 cell line assayed in the above Figure. The rationale behind assessing viability is to demonstrate that the compounds are not simply toxic in a non-specific manner, but rather that they exerted quantitative, measurable effects on the biology of hepatic stellate cells through specific molecular interactions.

Figure 3:
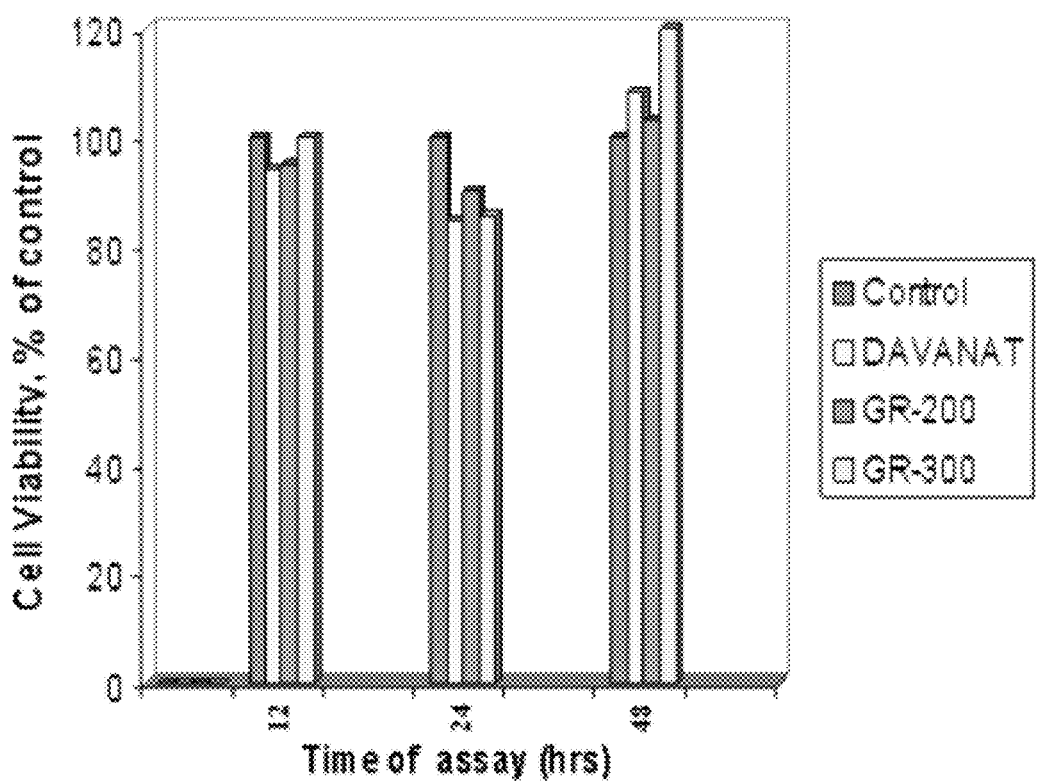
FIG. 3 shows the cell viability, treatments versus control untreated.

Obtained results showed that the significantly decreased expression of fibrosis markers was not due to decreased cell viability (FIG. 3) but rather due to an actual effect on mRNA expression. This Figure shows results of the MTT viability test for human hepatic stellate cell (HSC) line LX2 in the absence of polysaccharides as control, and in the presence of Davanat (1 mg/ml), GR-200 and GR-300 (0.1 mg/ml) (bar on the right). The data show that none of the three polysaccharides significantly effects the cell viability within error margin (typically 2% to 10% in these experiments).

Similarly, there was no significant effect of any of the three polysaccharides on cell LX2 proliferation, measured using $^3$H-Thymidine incorporation assay (Figure below).

Figure 4:
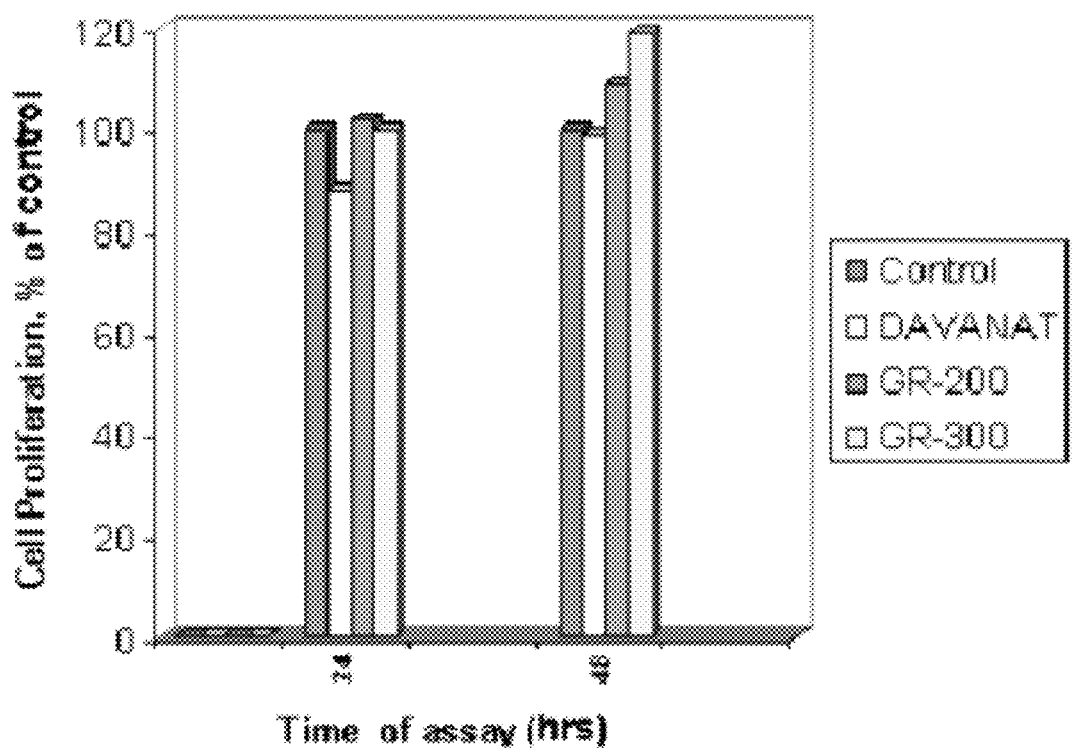
FIG. 4 shows the proliferation results of 3 galacto-polysaccharides on hepatic stellate cell (LX2 Cell line) using $^3$H-thymidine incorporation assay.

The results (FIG. 4) shows human hepatic stellate cell (HSC) line LX2 proliferation test using 3H-Thymidine incorporation assay in the absence of polysaccharides as control, and in the presence of 1 mg/ml DAVANAT, GR-200 or GR-300. The data show that none of the three polysaccharides significantly effects the cell proliferation within error margin (typically 10% to 30% in these experiments)

One can see that the galacto-rhamnogalacturonate from apple showed downregulation of a full panel of activation-related mRNAs, indicating a global effect on slowing down stellate cell specific activation. This is a manifestation of fibrotic process slowing down or even reversing.

EXAMPLE 3

In-Vivo Studies of the Admixture of the Present Invention in Model Animals

Pathogen-free male Wistar rats were housed at a constant temperature and supplied with laboratory chow and water ad libitum. Thioacetamide (TAA, from Wako Pure Chemical Co., Osaka, Japan) was used to induce Liver Fibrosis Model. The induction regimen and dosage was 50 mg/body, intraperitoneally administrated twice a week into rats (n=8-15) for up to 8 weeks. The admixture was administered either intraperitoneally or orally every day for 6 weeks. For testing reversibility of disease the admixture was administered either intraperitoneally or orally during the last 3-4 weeks of the induction period. 24-48 after the final treatment, the animals were anesthetized, and the peritoneal cavity was opened. The liver was perfused with phosphate-buffered saline via the portal to remove all blood from the whole liver lobules. Subsequently, part of the liver was treated with 10% formaldehyde and used for histologic examination. The remaining part was frozen in liquid nitrogen and stored at 80° C. for fibrosis markers analysis.

In other animal model fibrosis and cirrhosis were induced by Bile Duct Ligation. Rats were laparotomized and the common bile ducts were ligated at two different sites.

The rats were administered with the admixture—in this example including corticosteroid (10 mg/body)—intraperitoneally every day for 2 weeks. The results were that treatment with the admixture either intraperitoneally or orally suppressed fibrosis of the liver by at least 50% versus control untreated animals.

What is claimed is:
1. A method comprising the steps of:
   Obtaining a composition for parenteral administration comprising a selectively depolymerized galactomannan compound in an acceptable pharmaceutical carrier, wherein the selectively depolymerized galactomannan compound is a poly-β-1,4-mannan backbone, with galactose side substituents bound via α-1,6-glycoside linkages; and
   Administering to a subject having at least one of the following: chronic liver disease associated with the development of fibrosis, established liver fibrosis, or cirrhosis an effective dose of the composition for parenteral administration that results in at least one of the following:
   Inhibition or slowing down of progression of liver fibrosis or cirrhosis or reduction of established liver fibrosis or cirrhosis based on evidence comprising reduction of the level of biochemical markers of liver fibrosis, non invasive testing of liver fibrosis or cirrhosis or liver histologic grading of fibrosis or cirrhosis;

wherein, when the composition for parenteral administration is utilized to treat LX2 immortalized human hepatic stellate cells in a MTT cell viability assay, the assay treatment results in substantially no decreased viability of activated hepatic stellate cells following administration of the composition.

2. The method of claim 1, wherein the selectively depolymerized galactomannan compound has a molecular weight between 2 kD and 600 kD.

3. The method of claim 1, wherein the selectively depolymerized galactomannan compound has a mannose to galactose ratio of 1.7:1.

4. The method of claim 1, wherein the selectively depolymerized galactomannan compound has a mannose to galactose ratio of 2.2:1.

5. The method of claim 1, wherein the selectively depolymerized galactomannan compound has a mannose to galactose ratio of 2.6:1.5.

6. The method of claim 1, wherein the selectively depolymerized galactomannan compound has a mannose to galactose ratio of 2.2:0.9.

7. The method of claim 1, wherein the selectively depolymerized galactomannan compound has a mannose to galactose ratio of 1.13:1.

8. The method of claim 1, further comprising obtaining the selectively depolymerized galactomannan compound from *Cyamopsis tetragonoloba*.

9. A method comprising the steps of:

Obtaining a composition for parenteral administration comprising a selectively depolymerized galactomannan compound in an acceptable pharmaceutical carrier, wherein the selectively depolymerized galactomannan compound consists of a poly-β-1,4-mannan backbone, with side substituents bound via α-1,6-glycoside linkages and has a molecular weight between 2 kD and 600 kD; and Administering to a subject having at least one of the following: chronic liver disease associated with the development of fibrosis, established liver fibrosis, or cirrhosis an effective dose of the composition for parenteral administration that results in at least one of the following:

Inhibition or slowing down of progression of liver fibrosis or cirrhosis or reduction of established liver fibrosis or cirrhosis based on evidence comprising reduction of the level of biochemical markers of liver fibrosis, non invasive testing of liver fibrosis or cirrhosis or liver histologic grading of fibrosis or cirrhosis; or reduction in the medical consequences of liver fibrosis or cirrhosis;

wherein, when the composition for parenteral administration is utilized to treat LX2 immortalized human hepatic stellate cells in a MTT cell viability assay, the assay treatment results in substantially no decreased viability of activated hepatic stellate cells following administration of the composition.

* * * * *